United States Patent [19]
Adachi et al.

[11] Patent Number: 6,147,031
[45] Date of Patent: Nov. 14, 2000

[54] BENZOYLPYRAZOLE COMPOUNDS, INTERMEDIATE PREPARING THEREFOR AND HERBICIDES

[75] Inventors: Hiroyuki Adachi; Katsunori Tanaka, both of Odawara; Akihiro Takahashi, Ohi-machi; Masami Koguchi, Odawara, all of Japan

[73] Assignee: Nippon Soda Co., Ltd., Tokyo, Japan

[21] Appl. No.: 09/202,204

[22] PCT Filed: Oct. 29, 1998

[86] PCT No.: PCT/JP98/04898

§ 371 Date: Dec. 8, 1998

§ 102(e) Date: Dec. 8, 1998

[87] PCT Pub. No.: WO99/23094

PCT Pub. Date: May 14, 1999

[30] Foreign Application Priority Data

Oct. 30, 1997 [JP] Japan ................................. 9-299208

[51] Int. Cl.[7] .......................... A01N 43/80; C07D 261/02
[52] U.S. Cl. ............................ 504/271; 548/240
[58] Field of Search .................... 504/271, 280, 504/282; 548/364.1, 240

[56] References Cited

U.S. PATENT DOCUMENTS 5,834,402 11/1998 Von Deyn et al. ...................... 504/271
5,846,907 12/1998 Von Deyn et al. ...................... 504/221

FOREIGN PATENT DOCUMENTS

WO 96/26206 8/1996 WIPO .
WO 97/41105 11/1997 WIPO .
WO 98/31681 7/1998 WIPO .
WO 98/31682 7/1998 WIPO .

*Primary Examiner*—Deborah C. Lambkin
*Attorney, Agent, or Firm*—Joseph C. Mason, Jr.; Dennis G. LaPointe; Mason & Associates, PA

[57] ABSTRACT

A compound represented by the general formula [I]

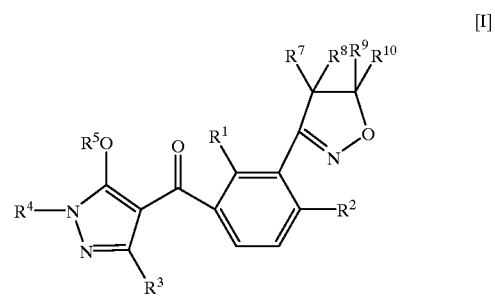

(wherein $R^1$ is a $C_1$–$C_6$ alkyl group; $R^2$ is a $C_1$–$C_6$ alkylsulfonyl group and the like; $R^3$ and $R^4$ are each independently hydrogen or a $C_1$–$C_6$ alkyl group; $R^5$ is hydrogen or a benzyl group or the like; $R^7$, $R^8$, $R^9$ and $R^{10}$ are each independently hydrogen or a $C_1$–$C_6$ alkyl group.) or a herbicide containing a salt thereof, intermediate preparing therefor, and the said compound.

3 Claims, No Drawings

BENZOYLPYRAZOLE COMPOUNDS, INTERMEDIATE PREPARING THEREFOR AND HERBICIDES

This application is a 371 of PCT/JP98/04898 Oct. 29, 1998.

TECHNICAL FIELD

The present invention relates to a novel pyrazole compound substituted with a benzoyl group at the 4 position of the pyrazole ring and a herbicide.

BACKGROUND ART

For culturing agrohorticultural crops, many herbicides have been used to control weeds, which required great labor. Herbicides applied, however, have caused chemical injuries on crops, or remained in or polluted the environment. It is therefore wanted to develop chemicals firmly effective at a smaller dosage thereof and applicable safely. As herbicides having a pyrazole skeleton substituted by a benzoyl group at the 4 position of the pyrazole ring, Tokkaihei(Japanese Patent Laid-Open Hei) No. 2-173 has disclosed compounds represented by General formula [A]

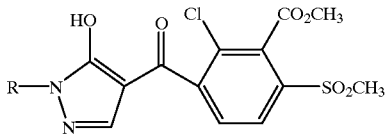

WO93/18031 Gazette has disclosed compounds represented by formula [B]

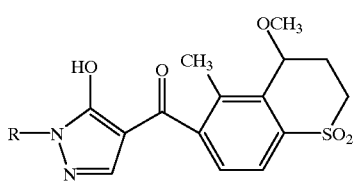

WO96/26206 Gazette has disclosed compounds represented by formula [C].

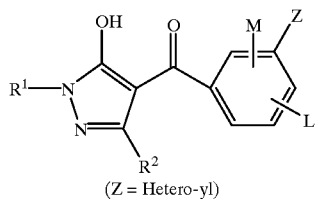

(Z = Hetero-yl)

It is an object of this invention to provide a herbicide that can be advantageously synthesized on an industrial scale, is firmly effective at a lower dosage, and selectively work on weeds without damaging crops.

DISCLOSURE OF THE INVENTION

That is to say, the present invention is directed to a compound represented by General formula [I]

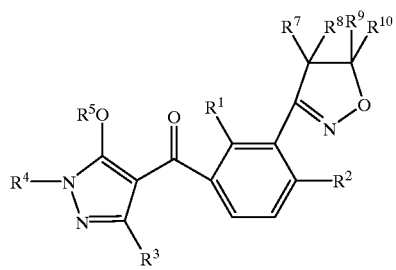

[wherein $R^1$ is a $C_1$–$C_6$ alkyl group; $R^2$ is a $C_1$–$C_6$ alkylthio group or a $C_1$–$C_6$ alkylsulfonyl group; $R^3$ and $R^4$ are each independently hydrogen or a $C_1$–$C_6$ alkyl group; $R^5$ is hydrogen or a group selected from the group represented by the following formula

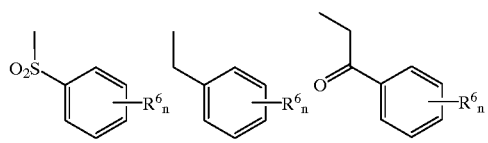

(where $R^6$ is halogen, a $C_1$–$C_6$ alkyl group or a $C_1$–$C_6$ alkoxy group; and n is 0, 1, 2, 3, 4 or 5); $R^7$, $R^8$, $R^9$ and $R^{10}$ are each independently hydrogen or a $C_1$–$C_6$ alkyl group; and ($R^7$ or $R^8$) and ($R^9$ or $R^{10}$) may form a single bond], or a salt thereof, and a herbicide containing one or more of the said compounds as active ingredients.

In General formula [I] illustrated above, $R^1$ is a $C_1$–$C_6$ alkyl group, such as methyl, ethyl, propyl, isopropyl, n-butyl, s-butyl and t-butyl. $R^2$ is a $C_1$–$C_6$ alkylthio group, such as methylthio, ethylthio, propylthio and isopropylthio or a $C_1$–$C_6$ alkylsulfonyl group, such as methylsulfonyl, ethylsulfonyl, propylsulfonyl and isopropylsulfonyl.

$R^3$ and $R^4$ are each independently hydrogen or a $C_1$–$C_6$ alkyl group, such as methyl, ethyl, propyl, isopropyl, n-butyl, s-butyl and t-butyl.

$R^5$ is hydrogen or the group represented by the above formula. Examples include a phenylsulfonyl group which may have substituent $R^6$, a benzyl group which may have substituent $R^6$, and a phenacyl group which may have substituent $R^6$.

Preferred examples include phenylsulfonyl, tosyl, 2,4,6-trimethylphenylsulfonyl, benzyl, 4-chlorobenzyl, 4-methylbenzyl, 4-methoxybenzyl, phenacyl, 4-methylphenacyl, and 3,5-dichlorophenacyl.

$R^6$ is hydrogen, halogen such as fluorine, chlorine and bromine; a $C_1$–$C_6$ alkyl group such as methyl, ethyl, propyl, isopropyl, n-butyl, s-butyl and t-butyl; or a $C_1$–$C_6$ alkoxy group such as methoxy, ethoxy, propoxy, isopropoxy, butoxy and t-butoxy.

$R^7$, $R^8$, $R^9$ and $R^{10}$ are each independently hydrogen or a $C_1$–$C_6$ alkyl group, such as methyl, ethyl, propyl, isopropyl, n-butyl, s-butyl and t-butyl. ($R^7$ or $R^8$) and ($R^9$ or $R^{11}$) may form a single bond.

Further, the present invention provides a benzoic acid or a benzoic acid ester which are raw materials of the said compounds represented by the above general formula [I]; a general formula (1)

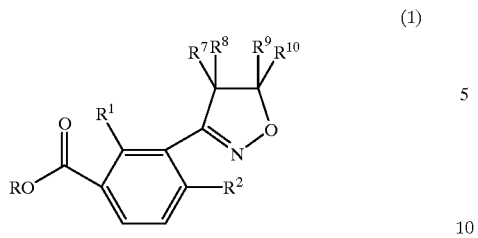

(wherein $R^1$, $R^2$, $R^7$ to $R^{10}$ are as defined above, and R is hydrogen or a $C_1$–$C_6$ alkyl group.).

$R^1$, $R^2$, $R^7$ to $R^{10}$ are as defined above in a general formula (1).

R is hydrogen or a straight chain or branching $C_1$–$C_6$ alkyl group such as methyl, ethyl, propyl, isopropyl, butyl, sec-butyl, tert-butyl, pentyl, hexyl or the like.

BEST MODE OF EMBODYING THE INVENTION

The compounds of this invention can be prepared according to the following reaction scheme:

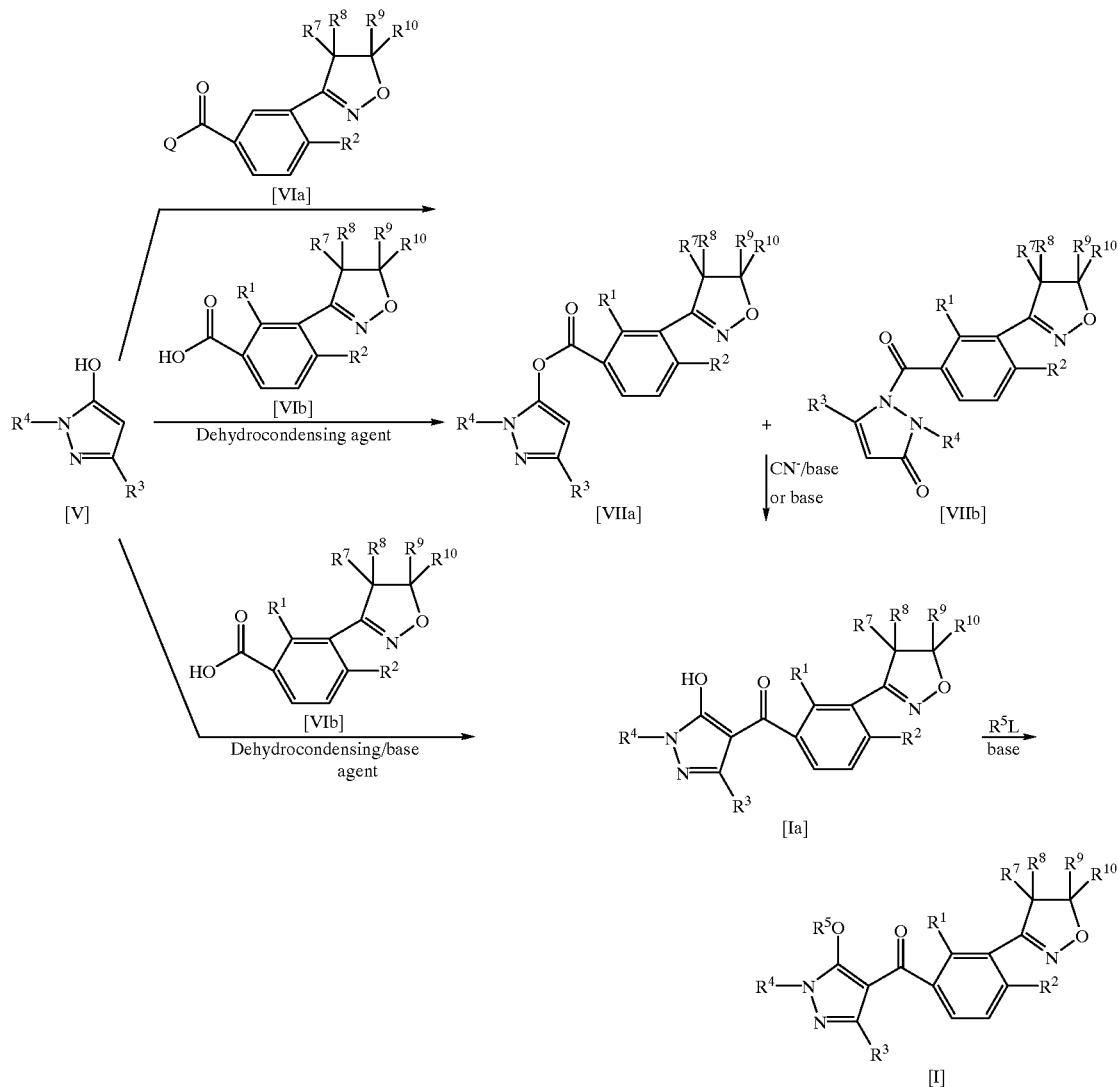

(wherein $R^1$ to $R^5$ and $R^7$ to $R^{11}$ are as defined above. Q is halogen, an alkylcarbonyloxy group, an alkoxycarbonyloxy group or a benzoyloxy group, and L is halogen.)

In the process illustrated above, compounds of formulas [VIIa] and [VIIb] can be prepared by reacting one mole of each of compounds of formulas [V] and [VIa] (Q is as defined above), or using an excessive amount of one of them to react with the other, in the presence of one mole or an excessive amount of a base.

Examples of bases used for this reaction include alkali metal hydroxides such as KOH and NaOH, alkali metal carbonates such as sodium carbonate and potassium carbonate, hydroxides of alkaline earth metals such as calcium hydroxide and magnesium hydroxide, carbonates of alkaline earth metals such as calcium carbonate, tri($C_1$–$C_6$ alkyl) amines such as triethylamine and diisopropylethylamine, organic bases such as pyridine, and sodium phosphate.

Examples of solvents used for the reaction include water, dichloromethane, chloroform toluene, ethyl acetate, dimethylformamide (DMF), tetrahydrofuran (THF), dimethoxy ethane (DME) and acetonitrile.

The reaction mixture for the reaction described above is stirred at 0° C.~50° C. until the reaction is completed. In addition, the reaction can be carried out in a two-phase system, using a phase-transfer catalyst such as a quaternary ammonium salt.

Furthermore, the compounds of formulas [VIIa] and [VIIb] may also be prepared by reacting compounds of formulas [V] and [VIb] in the presence of a dehydrocondensing agent such as dicyclohexylcarboimide (DCC).

Solvents used for this reaction include dichloromethane, chloroform, toluene, ethyl acetate, DMF, THE, DME, acetonitrile and t-pentyl alcohol.

The reaction mixture is stirred at −10° C.~50° C. until the reaction is completed. The reaction mixture is treated by a usual process.

The compounds of formulas [VIIa] and [VIIb] are used as a mixture in the following rearrangement reaction.

The rearrangement reaction is carried out in the presence of a cyano compound and a mild base: one mole of the compounds of formulas [VIIa] and [VIIb] is reacted with 1 to 4 moles, preferably 1 to 2 moles, of a base and 0.01 mole to 1.0 mole, preferably 0.05 mole to 0.2 mole, of a cyano compound to give a compound represented by [Ia].

Examples of bases used for the said reaction include alkali metal hydroxides such as KOH and NaOH, alkali metal carbonates such as sodium carbonate and potassium carbonate, hydroxides of alkaline earth metals such as calcium hydroxide and magnesium hydroxide, carbonates of alkaline earth metals such as calcium carbonate, tri($C_1$–$C_6$ alkyl) amines such as triethylamine and diisopropylethylamine, organic bases such as pyridine, and sodium phosphate.

Examples of cyano compounds are potassium cyanide, sodium cyanide, acetone cyanohydrin, hydrogen cyanide and polymers containing potassium cyanide. The reaction is completed in a shorter period of time if a small amount of a phase transfer catalyst, such as crown ether, is added.

The reaction is carried out at a temperature lower than 80° C., preferably in the temperature range from room temperature to 40° C. Examples of solvents used for the reaction include 1,2-dichloroethane, toluene, acetonitrile, dichloromethane, chloroform, ethyl acetate, DMF, methyl isobutyl ketone, THF and DME.

The rearrangement reaction may be carried out in an inert solvent in the presence of a base such as potassium carbonate, sodium carbonate, triethylamine or pyridine. An amount of a base used in the reaction is 0.5~2.0 moles to that of the compounds of formulas [VIIa] and [VIIb]. Examples of solvents include THF, dioxane, t-pentyl alcohol and t-butyl alcohol. Reaction temperature is preferably from room temperature to the boiling point of a solvent used.

Furthermore, the compound of formula [Ia] can also be prepared from the compounds of formulas [V] and [VIb] with the use of a base together with a dehydrocondensing agent, such as DCC, without isolating the compounds of formulas [VIIa] and [VIIb]. Examples of bases used for this reaction are potassium carbonate, sodium carbonate, triethylamine and pyridine. An amount of a base used is preferably 0.5~2.0 moles to that of the compound of formula [V]. Examples of solvents include THF, dioxane, t-pentyl alcohol and t-butyl alcohol. Reaction temperature is preferably from room temperature to the boiling point of a solvent used.

The compound of formula [I] may be prepared by reacting a compound of formula [Ia] with a compound represented by $R^5L$ ($R^5$ and L are as defined above) in the presence of a base. Examples of bases used for this reaction include alkali metal hydroxides such as KOH and NaOH, alkali metal carbonates such as potassium carbonate and sodium carbonate, hydroxides of alkaline earth metals such as calcium hydroxide, carbonates of alkaline earth metals such as calcium carbonate, tri($C_1$–$C_6$ alkyl)amines such as triethylamine and diisopropylethylamine, organic bases such as pyridine, and sodium phosphate.

Examples of solvents for the reaction include dichloromethane, chloroform, toluene, ethyl acetate, DMF, THF, DME and acetonitrile.

The reaction is carried out in a temperature range from 0° C. to the boiling point of a solvent used until the reaction is completed. The compound of formula [I] can also be prepared by a reaction in a two-phase system of water and a water-insoluble solvent among the above-mentioned solvents, with the use of a phase-transfer catalyst such as a quaternary ammonium salt.

5-Hydroxypyrazole compounds represented by General formula [V] may be prepared according to the following processes which have been disclosed, for example, in Tokkaisho(Japanese Patent Laid-Open Sho) No. 62-234069 or Tokkaihei(Japanese Patent Laid-Open Hei) No. 3-44375.

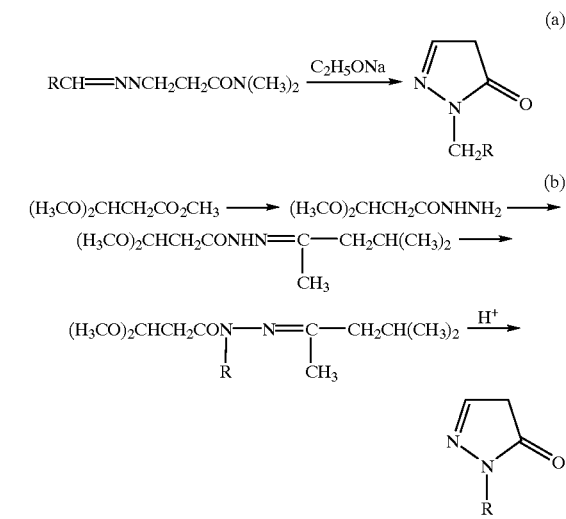

A compound represented by General formula (1), an important intermediate for preparing the compounds of this invention, may be prepared according to the following reaction scheme:

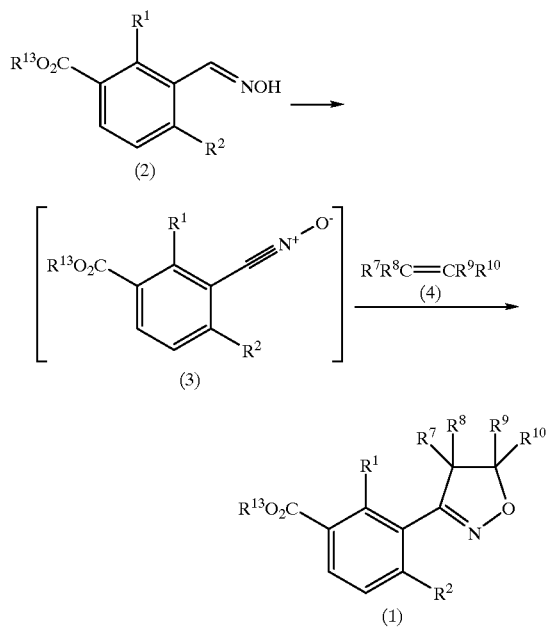

(wherein $R^1$, $R^2$, $R^7$, $R^8$, $R^9$ and $R^{10}$ are as defined above and $R^{13}$ is a lower alkyl group.)

A dihydroisoxazole compound represented by General formula (1) may be prepared in a way that an aldoxime compound of formula (2) is reacted with a halogenating agent such as chlorine, bromine, N-chlorosuccinimide (NCS) or N-bromosuccinimide (NBS), in a solvent including a hydrocarbon such as benzene or toluene, an ether such as THF or dioxane, a nitrile such as acetonitrile, or DMF, at temperature between −10 and 50° C., followed by a reaction with a base including an organic base such as triethylamine or a carbonate such as sodium hydrogen carbonate or potassium carbonate, to give a nitrile oxide compound of formula (3). The obtained nitrile oxide is then reacted with a compound represented by General formula (4) ( $R^7$, $R^8$, $R^9$ and $R^{10}$ are as defined above, and preferably hydrogen or methyl), at the atmospheric pressure or under pressure using a pressurizing vessel such as an autoclave, in the presence of the compound of formula (4) at temperature from −10° C. to 150° C. The said nitrile oxide compound of formula (3) can be prepared by reacting an aldoxime compound of formula (2) with a hypohalogen acid salt such as sodium hypochlorite.

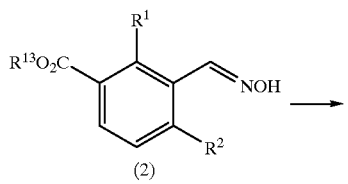

(wherein $R^1$, $R^2$, $R^{13}$ are as defined above, and $R^{11}$ and $R^{12}$ correspond to the above-mentioned $R^7$, $R^8$, $R^9$ or $R^{10}$.)

An isoxazole compound represented by General formula (7) may be prepared in a way that the aldoxime compound of formula (2) is reacted with a halogenating agent such as chlorine, bromine, N-chlorosuccinimide (NCS) or N-bromosuccinimide (NBS), in a solvent including a hydrocarbon such as benzene or toluene, a halogenated hydrocarbon such as dichloromethane or chloroform an ether such as THF or dioxane, a nitrile such as acetonitrile, or DMF, at temperature between −10 and 50° C., followed by a reaction with a base including an organic base such as triethylamine or a carbonate such as sodium carbonate or potassium carbonate, to give a nitrile oxide compound of formula (3). The obtained nitrile oxide is then reacted with a substituted vinyl acetate of formula (8) or substituted acetylene of formula (9) in a temperature range from −10° C. to the boiling point of a solvent used.

The isoxazole compound of formula (7) may also be prepared by reacting the said aldoxime compound of formula (2) with a halogenating agent to give a halogenated compound. The obtained halogenated compound is then reacted with a base mentioned above, in the presence of the substituted vinyl acetate of formula (8) or substituted acetylene of formula (9).

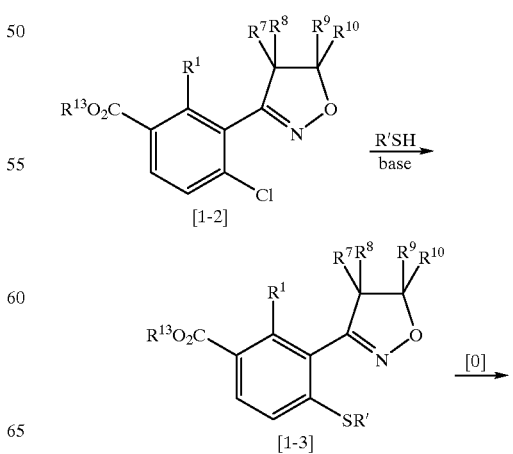

-continued

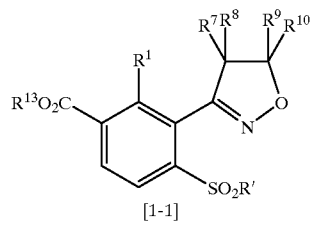

[1-1]

(wherein $R^1$, $R^7$, $R^8$, $R^9$, $R^{10}$ and $R^{13}$ are as defined above and R' is a $C_1$–$C_6$ alkyl group.)

Benzoic acid compounds represented by formula (1-1) may be produced by reacting a 4-Cl compound represented by formula (1-2) with a thiol represented by R'SH in the presence of a base to give a 4-SR' compound represented by formula (1-3), followed by the oxidation of the 4-SR' compound.

Examples of bases used for this reaction are alkali metal hydroxides such as sodium hydroxide and potassium hydroxide, metal alkoxides such as sodium methoxide and sodium ethoxide, carbonates such as sodium carbonate and potassium carbonate, hydrides such as sodium hydride, and organic bases such as trieythylamine, diisopropylethylamine, 1,8-diazabicyclo[5.4.0]unde-7-cene (DBU) and pyridine. Examples of solvents used for the reaction are alcohols such as methanol and ethanol, ethers such as THF and DME, amides such as DMF and dimethylacetamide, hydrocarbons such as benzene, toluene and xylene, dimethylsulfoxide (DMSO), and acetonitrile.

The following oxidation reaction is carried out, using an oxidizing agent including a peroxy acid such as hydrogen peroxide, peracetic acid, perbenzoic acid and m-chloroperbenzoic acid, or a hypochlorite such as sodium hypochlorite or potassium hypochlorite, in an inert solvent including water, an organic acid such as acetic acid or a halogenated hydrocarbon such as dichloromethane, chloroform or carbon tetrachloride. The reaction proceeds smoothly in a temperature range from room temperature to the boiling point of a solvent used.

If a compound of formula [I] contains a free hydroxyl group, a salt thereof, particularly an agrohorticulturally acceptable salt, can be derived from the said compound. Examples of agrohorticulturally acceptable salts are salts of sodium, potassium calcium and ammonium.

Examples of ammonium salts are salts with ions of formula: $N^+RaRbRcRd$ (where Ra, Rb, Rc and Rd are each independently hydrogen or, as the case may be, a $C_1$–$C_{10}$ alkyl substituted with such a group as hydroxy). In case any of Ra, Rb, Rc and Rd is a substituted alkyl, as the case may be, it preferably has 1 to 4 carbons.

These derivatives can be prepared by usual processes.

The compound of formula [Ia] of this invention may exist in the form of tautomers as many as shown in the following. These tautomers are all within the scope of the present invention.

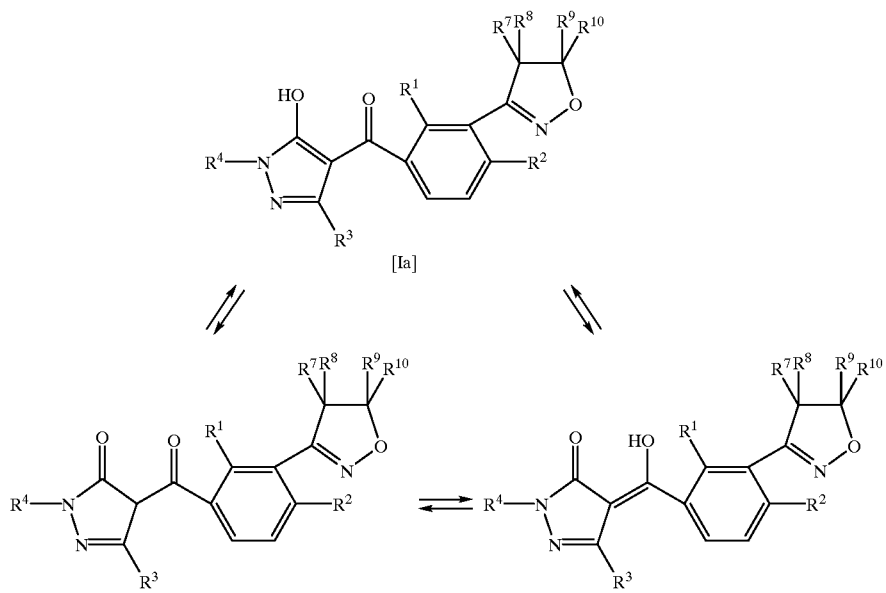

(wherein $R^1$, $R^2$, $R^3$, $R^4$, $R^7$, $R^8$, $R^9$ an $R^{10}$ are as defined above.)

The compounds of this invention and various intermediates are obtained by usual post-treatment after reactions are completed.

The structure of the compounds of the present invention and various intermediates were determined by using IR, NMR, MS and other available means.

Herbicide

The compounds of the present invention have high herbicidal activity in either soil or foliage treatment under the conditions of upland crop farming. They are effective on various upland weeds such as crabgrass, cyperaceous weeds, velvetleaf and pigweed. Compounds that work on weeds selectively without damaging crops, such as corn, wheat, soybean and cotton, are also included in the compounds of the present invention.

The compounds of this invention also include those having activity to control plant growth, such as growth retarding, of useful plants such as agricultural crops, ornamental foliage plants and fruit trees.

The compounds of this invention have excellent herbicidal action on various lowland weeds such as barnyard grass, *Cyperus difformis, Sagittaria trifolia* and *Scirpus juncoides*. Compounds that work on weeds selectively without damaging rice plants are also included in the compounds of the present invention.

Moreover, the compounds of this invention may be applied to control weeds in such places as orchards, lawns, railway passages and vacant lands.

The compounds of the present invention include those having actions to control plant growth, and bactericidal, insecticidal and acaricidal activities.

The herbicidal composition according to the present invention contains one or more compounds of the present invention as active ingredients. When actually applied, the compound of the present invention can be used in a pure form without adding any other components. The compounds of the present invention can be used in a form of formulation usually employed for agricultural chemicals, such as wettable powder, granules, powder, emulsifiable concentrates, water soluble chemicals, suspensions and floables, when they are used as agricultural chemicals. When an agricultural chemical is to form a solid formation, examples of additives and carriers include vegetable powder such as soybean powder and wheat powder, fine mineral powder such as diatomaceous earth, apatite, gypsum, talc, bentonite, pyrophylite and clay, and organic and inorganic compounds such as sodium benzoate, urea and Glauber's salt. In the case of forming a liquid formulation, petroleum fractions such as kerosine, xylene and solvent naphtha, cyclohexane, cyclohexanone, DMF, DMSO, alcohol, acetone, trichloroethylene, methyl isobutyl ketone, mineral oils, vegetable oils and water may be used as a solvent. In order to make these formulations uniform and stable, surface active agents may be added, if required. Any surface active agent may be used without particular restrictions. Examples of surfactants include non-ionic surface active agents such as polyoxyethylene added alkylphenyl ethers, polyoxyethylene added alkyl ethers, polyoxyethylene added higher fatty acid esters, polyoxyethylene added sorbitan higher fatty acid esters and polyoxyethylene added tristyrylphenyl ethers, sulfates of polyoxyethylene added alkylphenyl ethers, alkylbenzene sulfonates, higher alcohol sulfates, alkyl sulfates, alkylnaphthalene sulfonates, polycarboxylic acid salts, lignin sulfonates, condensation products of alkylnaphthalene sulfonates with formaldehyde, and copolymers of isobutylene and maleic anhydride.

The concentration of an active ingredient in the herbicide of the present invention varies depending on a formulation form described above. For example, an active ingredient is 5~90% by weight (herein after abbreviated simply as %), preferably 10~85%, in wettable powder; 3~70%, preferably 5~60%, in an emulsifiable concentrate; and 0.01~50%, preferably 0.05~40%, in a granule.

The wettable powder or emulsifiable concentrate, thus obtained, is diluted with water to a prescribed concentration in order to use as a suspension or an emulsion. Granules are used as they are. The suspension, emulsion or granules may be applied by spraying or admixing before or after weeds germinate. When a herbicide of this invention is actually applied, an appropriate amount of the active ingredient is 0.1 g or more per hectare.

Furthermore, a herbicide of the present invention may be used as a mixture with known agents such as fungicides, insecticides, acaricides, other herbicides, plant growth regulators and fertilizers. In particular, if a herbicide of this invention is mixed with another herbicide, it is possible to reduce amounts of chemicals used. In addition, the employment of the herbicide of the present invention leads to the reduction of labor as well as much higher herbicidal action thanks to the synergistic effect of the mixed chemicals. In this case, it is also possible to mix a herbicide of this invention with two or more of known herbicides.

Examples of chemicals suitable to mix with a herbicide of the present invention include anilide-containing herbicides such as diflufenican and propanil; chloroacetanilide-containing herbicides such as alachlor and pretilachlor; aryloxyalkanic acid-containing herbicides such as 2,4-D and 2,4-DB; aryloxyphenoxyalkanic acid-containing herbicides such as diclofop-methyl and fenoxaprop-ethyl; arylcarboxylic acid-containing herbicides such as dicamba and pyrithiobac-sodium; imidazolinone-containing herbicides such as imazaquin and imazethapyr; urea-containing herbicides such as diuron and isoproturon; carbamate-containing herbicides such as chlorproham and phenmedipham; thiocarbamate-containing herbicides such as thiobencarb and EPTC; dinitroaniline-containing herbicides such as trifluralin and pendimethalin; diphenyl ether-containing herbicides such as acifluorfen and fomesafen; sulfonylurea-containing herbicides such as bensulfuronmethyl and nicosulfuron; triazinone-containing herbicides such as metribuzin and metamitron; triazine-containing herbicides such as atrazine and cyanazine; triazopyrimidine-containing herbicides such as flumetsulam; nitrile-containing herbicides such as bromoxynil and dichlobenil; phosphoric acid-containing herbicides such as glyphosate and glufosinate; quaternary ammonium salt-containing herbicides such as paraquat and difenzoquat; cyclic imide-containing herbicides such as flumiclorac-pentyl and fluthiacet-methyl; other herbicides such as isoxaben, ethofumesate, oxadiazon, quinclorac, clomazone, sulcotrione, cinmethylin, dithiopyr, pyrazolate, pyridate, flupoxam bentazone and benfuresate; and cyclohexadione-containing herbicides such as sethoxydim and tralkoxydim. A vegetable oil and an oil concentrate may be added to a mixture of these herbicides.

EXAMPLES

The compounds of the present invention are described further with reference to the following reference examples and examples.

Reference Example 1

Preparation of methyl 3-bromomethyl-4-methylsulfonyl-2-methylbenzoate

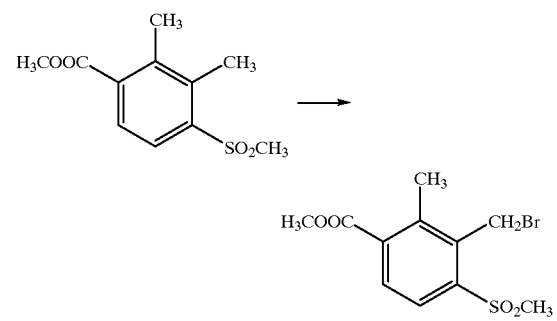

29.69 g of methyl 2,3-dimethyl-4-methylsulfonylbenzoate was dissolved in 260 ml of carbon tetrachloride, and 22.93 g of NBS and 1.0 g of benzoyl peroxide were added to heat at reflux for 2.5 hours. The reaction solution was cooled down, and insoluble matter was separated by filtration. The filtrate was concentrated under reduced pressure to give 56.58 g of viscous oil. The obtained oil was purified by column chromatography on silica gel with n-hexane/ethyl acetate=5/1 to give 18.98 g of the title compound as white crystals.

Reference Example 2

Preparation of methyl 3-formyl-4-methylsulfonyl-2-methylbenzoate

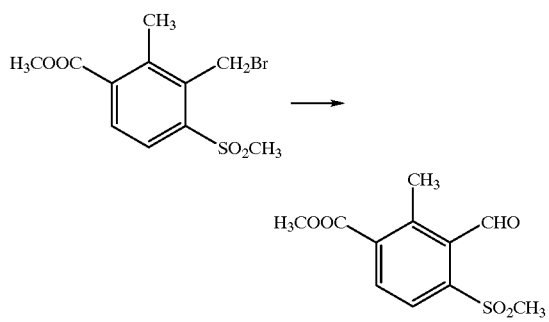

18.90 g of methyl 3-bromomethyl-4-methylsulfonyl-2-methylbenzoate was dissolved in 180 ml of acetonitrile, and 20.67 g of N-methylmorpholine oxide was added over 10 minutes at room temperature. The resulting solution was stirred at room temperature for an hour, poured into ice water, acidified with concentrated hydrochloric acid, and extracted with benzene. The organic layer was washed with water, then with a saturated sodium chloride solution, and dried over anhydrous magnesium sulfate. The solvent was distilled out under reduced pressure to give 11.59 g of the title compound as white crystals. The crude product was washed with ethanol to give white crystals of the title compound. m.p. 108~110° C.

Reference Example 3

Preparation of methyl 3-formyl-4-methylsulfonyl-2-methylbenzoate

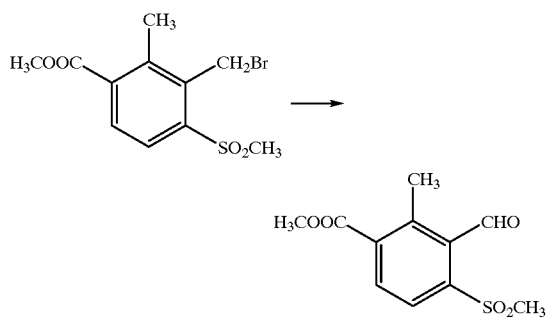

Into 20 ml of methanol was added 2.60 g of a methanol solution of 28% sodium methylate, and 1.30 g of 2-nitropropane was added dropwise at room temperature, followed by adding 4.40 g of methyl 3-bromomethyl-4-methylsulfonyl-2-methylbenzoate. The resulting solution was heated at reflux for an hour. After the reaction solution was cooled down, 50 ml of IN hydrochloric acid was added to the solution to extract with ethyl acetate. The organic layer was washed with a saturated sodium chloride solution and dried over anhydrous magnesium sulfate. The solvent was distilled out under reduced pressure to give 3.10 g of the title compound as crystals. m.p. 108~110° C.

Reference Example 4

Preparation of methyl 3-hydroxyiminomethyl-4-methylsulfonyl-2-methylbenzoate

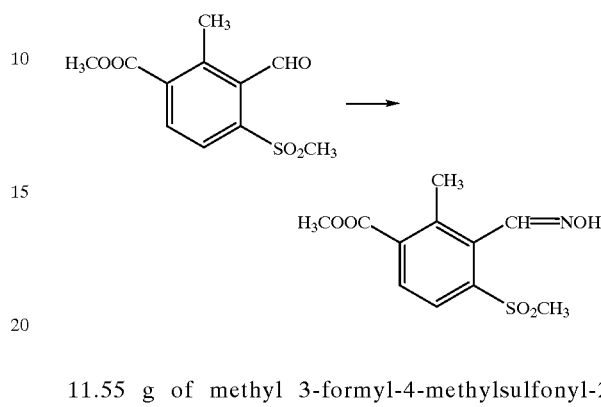

11.55 g of methyl 3-formyl-4-methylsulfonyl-2-methylbenzoate was dissolved in 100 ml of ethanol, and 4.70 g of hydroxylamine hydrochloride was added. The resulting solution was reacted for 1.5 hours at room temperature and further heated at reflux for an hour. The reaction solution was cooled down. Ethanol was then distilled out under reduced pressure. The obtained residue was dissolved in ethyl acetate. The ethyl acetate solution was washed with water and a saturated sodium chloride solution, and dried over anhydrous magnesium sulfate. The solvent was distilled out under reduced pressure to give 12.31 g of a crude product as viscous oil. The crude product was purified by column chromatography on silica gel with n-hexane/ethyl acetate=2/1 to give the title compound as white crystals. m.p. 123~129° C.

Example 1

Preparation of methyl 3-(4,5-dihydroisoxazol-3-yl)-4-methylsulfonyl-2-methylbenzoate

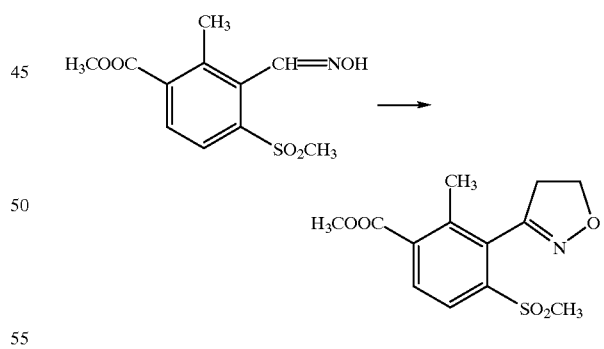

6.00 g of crude methyl 3-hydroxyiminomethyl-4-methylsulfonyl-2-methylbenzoate was dissolved in 100 ml of chloroform Chlorine was blown into the resulting solution, with stirring, for 35 minutes at −3~3° C. The solution was further stirred for 30 minutes at 0° C. Nitrogen gas was blown into the reaction solution to remove excessive chlorine. Further chloroform was distilled out under reduced pressure to give viscous oil. The obtained oil was dissolved in 90 ml of ether, and ethylene was blown in, with stirring, for 5 minutes at −10° C. Then 7 ml of triethylamine and 7 ml of ether were added dropwise at −10° C. Further ethylene was blown in for 20 minutes. The resulting reaction mixture was transferred to a 200 ml, stainless-steel autoclave, which was cooled beforehand, and stirred for 3.5 hours at 60~70° C. The reaction solution was cooled down, poured into water, acidified with hydrochloric acid, and extracted with ethyl acetate. The organic layer was washed with water, then with a saturated sodium chloride solution, and dried over anhydrous magnesium sulfate. The solvent was distilled out under reduced pressure. The obtained crude product was purified by column chromatography on silica gel with n-hexane/ethyl acetate=2/1 to give 3.20 g of the title compound as white crystals. m.p. 104~106.5° C.

Example 2

Preparation of 3-(4,5-dihydroisoxazol-3-yl)-4-methylsulfonyl-2-methylbenzoic acid

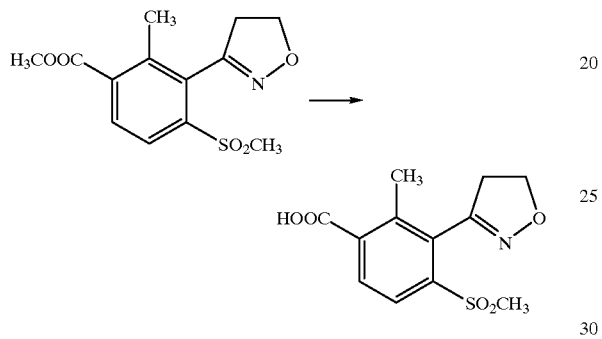

To 3.00 g of methyl 3-(4,5-dihydroisoxazol-3-yl)-4-methylsulfonyl-2-methylbenzoate were added 10 ml of ethanol and 20 ml of a 1N sodium hydroxide solution to stir at room temperature for 2 days. Ethanol was distilled out under reduced pressure. The remaining solution was acidified with hydrochloric acid and extracted with ethyl acetate. The organic layer was washed with water, then with a saturated sodium chloride solution, and dried over anhydrous magnesium sulfate. The solvent was distilled out under reduced pressure to give 2.75 g of the title compound as white crystals. m.p. 182~184.5° C.

Example 3

Preparation of methyl 3-(isoxazol-3-yl)-4-methylsulfonyl-2-methylbenzoate

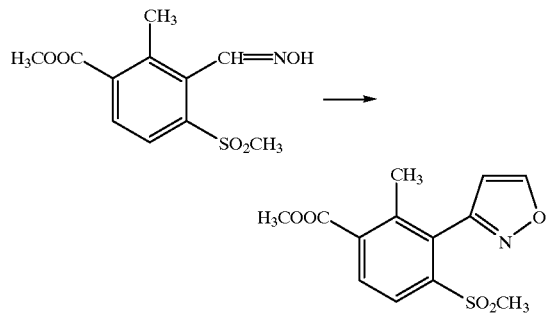

2.00 g of crude methyl 3-hydroxyiminomethyl-4-methylsulfonyl-2-methylbenzoate was dissolved in 35 ml of chloroform Chlorine gas was blown into the resulting solution, with stirring, for 30 minutes at −13~0° C. The solution was further stirred for 30 minutes at 0° C. Nitrogen gas was blown into the reaction solution to remove excessive chlorine. Chloroform was concentrated under reduced pressure to give a solid product. The obtained solid was dissolved in 50 ml of ether. Acetylene gas was blown in, with stirring, for 5 minutes at −11° C. Then 1.64 g of triethylamine dissolved in 5 ml of ether was added dropwise at −15~13.5° C. Further acetylene gas was blown in for 20 minutes at −15~13.5° C. The resulting reaction mixture was transferred to a 50 ml, stainless-steel autoclave, which was cooled beforehand, and stirred for 3.5 hours at 60~70° C. The reaction solution was cooled down, poured into water, and extracted with ethyl acetate. The organic layer was washed with water, then with a saturated sodium chloride solution, and dried over anhydrous magnesium sulfate. The solvent was distilled out under reduced pressure. The obtained residue was purified by column chromatography on silica gel with benzene/ethyl acetate=9/1 to give 0.82 g of the title compound as white crystals. m.p. 87~89° C.

Example 4

Preparation of 3-(isoxazol-3-yl)-4-methylsulfonyl-2-methylbenzoic acid

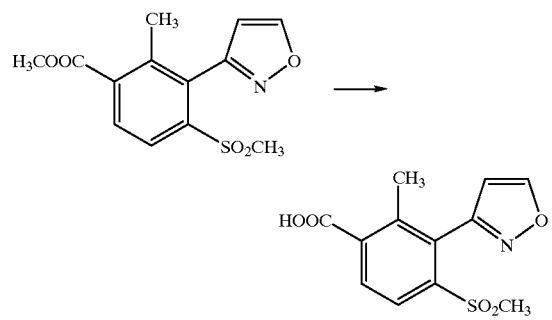

To 0.80 g of methyl 3-(isoxazol-3-yl)-4-methylsulfonyl-2-methylbenzoate were added 8 ml of ethanol and 8 ml of a 1N sodium hydroxide solution to stir at room temperature for 2 days. The reaction solution was poured into ice water, acidified with hydrochloric acid and extracted with ethyl acetate. The organic layer was washed with water, then with a saturated sodium chloride solution, and dried over anhydrous magnesium sulfate. The solvent was distilled out under reduced pressure to give 0.56 g of the title compound as white crystals. m.p. 150–151° C.

Examples of the compounds of the present invention, including those in the above examples, are shown in Table 1.

TABLE 1

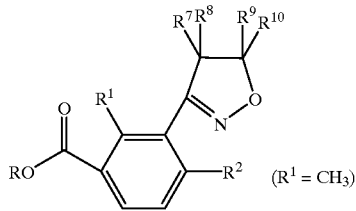

($R^1 = CH_3$)

| Compound No. | R | $R^2$ | $R^7$ | $R^8$ | $R^9$ | $R^{10}$ | Melting Point (° C.) |
|---|---|---|---|---|---|---|---|
| 1 | H | $SO_2CH_3$ | H | H | H | H | [182–184.5] |
| 2 | $CH_3$ | $SO_2CH_3$ | H | H | H | H | [104–106.5] |
| 3 | $C_2H_5$ | $SO_2CH_3$ | H | H | H | H | |
| 4 | $C_3H_7$ | $SO_2CH_3$ | H | H | H | H | |
| 5 | $i-C_3H_7$ | $SO_2CH_3$ | H | H | H | H | |
| 6 | $C_4H_9$ | $SO_2CH_3$ | H | H | H | H | |
| 7 | $t-C_4H_9$ | $SO_2CH_3$ | H | H | H | H | |
| 8 | H | $SO_2CH_3$ | H | H | $CH_3$ | H | [133–134] |
| 9 | $CH_3$ | $SO_2CH_3$ | H | H | $CH_3$ | H | [85–87] |
| 10 | $C_2H_5$ | $SO_2CH_3$ | H | H | H | H | |
| 11 | $C_3H_7$ | $SO_2CH_3$ | H | H | H | H | |
| 12 | $i-C_3H_7$ | $SO_2CH_3$ | H | H | H | H | |
| 13 | $C_4H_9$ | $SO_2CH_3$ | H | H | H | H | |
| 14 | $t-C_4H_9$ | $SO_2CH_3$ | H | H | H | H | |
| 15 | H | $SO_2CH_3$ | $CH_3$ | H | H | H | |
| 16 | $CH_3$ | $SO_2CH_3$ | $CH_3$ | H | H | H | |
| 17 | H | $SO_2CH_3$ | H | H | $C_2H_5$ | H | |
| 18 | $CH_3$ | $SO_2CH_3$ | H | H | $C_2H_5$ | H | |
| 19 | H | $SO_2CH_3$ | $CH_3$ | H | $CH_3$ | H | |
| 20 | $CH_3$ | $SO_2CH_3$ | $CH_3$ | H | $CH_3$ | H | |
| 21 | H | $SO_2CH_3$ | H | H | $i-C_3H_7$ | H | |
| 22 | $CH_3$ | $SO_2CH_3$ | H | H | $i-C_3H_7$ | H | |
| 23 | H | $SO_2CH_3$ | H | H | $CH_3$ | $CH_3$ | |
| 24 | $CH_3$ | $SO_2CH_3$ | H | H | $CH_3$ | $CH_3$ | |
| 25 | $C_2H_5$ | $SO_2CH_3$ | H | H | $CH_3$ | $CH_3$ | |
| 26 | H | $SO_2CH_3$ | H | H | $CH_3$ | $C_2H_5$ | |
| 27 | $CH_3$ | $SO_2CH_3$ | H | H | $CH_3$ | $C_2H_5$ | |
| 28 | H | $SO_2CH_3$ | H | H | $C_2H_5$ | $C_2H_5$ | |
| 29 | $CH_3$ | $SO_2CH_3$ | H | H | $C_2H_5$ | $C_2H_5$ | |
| 30 | H | $SO_2CH_3$ | $CH_3$ | $C_2H_5$ | H | H | |
| 31 | $CH_3$ | $SO_2CH_3$ | $CH_3$ | $C_2H_5$ | H | H | |
| 32 | H | $SO_2CH_3$ | $C_2H_5$ | $C_2H_5$ | H | H | |
| 33 | $CH_3$ | $SO_2CH_3$ | $C_2H_5$ | $C_2H_5$ | H | H | |
| 34 | H | $SO_2CH_3$ | $CH_3$ | $CH_3$ | H | H | |
| 35 | $CH_3$ | $SO_2CH_3$ | $CH_3$ | $CH_3$ | H | H | |
| 36 | H | $SO_2CH_3$ | H | H | H | H | |
| 37 | $CH_3$ | $SO_2CH_3$ | H | H | H | H | |
| 38 | H | $SO_2CH_3$ | H | H | H | H | |
| 39 | $CH_3$ | $SO_2CH_3$ | H | H | H | H | |
| 40 | H | $SO_2CH_3$ | H | H | H | H | |
| 41 | $CH_3$ | $SO_2CH_3$ | H | H | H | H | |
| 42 | $CH_3$ | $SO_2CH_3$ | H | H | H | H | |
| 43 | H | $SO_2CH_3$ | H | single bond | | H | [150–151] |
| 44 | $CH_3$ | $SO_2CH_3$ | H | single bond | | H | [87–89] |
| 45 | $C_2H_5$ | $SO_2CH_3$ | H | single bond | | H | |
| 46 | $i-C_3H_7$ | $SO_2CH_3$ | H | single bond | | H | |
| 47 | $C_4H_9$ | $SO_2CH_3$ | H | single bond | | H | |
| 48 | $t-C_4H_9$ | $SO_2CH_3$ | H | single bond | | H | |
| 49 | H | $SO_2CH_3$ | $CH_3$ | single bond | | H | |
| 50 | $CH_3$ | $SO_2CH_3$ | $CH_3$ | single bond | | H | |
| 51 | H | $SO_2CH_3$ | H | single bond | | $CH_3$ | [158–162] |
| 52 | $CH_3$ | $SO_2CH_3$ | H | single bond | | $CH_3$ | [100–105] |
| 53 | $C_2H_5$ | $SO_2CH_3$ | H | single bond | | $CH_3$ | |
| 54 | $i-C_3H_7$ | $SO_2CH_3$ | H | single bond | | H | |
| 55 | $C_4H_9$ | $SO_2CH_3$ | H | single bond | | H | |
| 56 | $t-C_4H_9$ | $SO_2CH_3$ | H | single bond | | H | |
| 57 | H | $SO_2CH_3$ | $CH_3$ | single bond | | $CH_3$ | |
| 58 | $CH_3$ | $SO_2CH_3$ | $CH_3$ | single bond | | $CH_3$ | |
| 59 | H | $SO_2CH_3$ | H | single bond | | $C_2H_5$ | |
| 60 | $CH_3$ | $SO_2CH_3$ | H | single bond | | $C_2H_5$ | |
| 61 | H | $SO_2CH_3$ | $C_2H_5$ | single bond | | H | |
| 62 | $CH_3$ | $SO_2CH_3$ | $C_2H_5$ | single bond | | H | |
| 63 | H | $SO_2CH_3$ | $CH_3$ | single bond | | $C_2H_5$ | |
| 64 | $CH_3$ | $SO_2CH_3$ | $CH_3$ | single bond | | $C_2H_5$ | |

TABLE 1-continued

[Structure with $R^1 = CH_3$]

| Compound No. | R | $R^2$ | $R^7$ | $R^8$ | $R^9$ | $R^{10}$ | Melting Point (° C.) |
|---|---|---|---|---|---|---|---|
| 65 | H | $SO_2CH_3$ | H | single bond | | $i-C_3H_7$ | |
| 66 | $CH_3$ | $SO_2CH_3$ | H | single bond | | $i-C_3H_7$ | |

Example 5

Preparation of 4-[3-(4,5-dihydroisoxazol-3-yl)-4-methylsulfonyl-2-methylbenzoyl]-5-hydroxy-1-methylpyrazole (Compound No. 1-1)

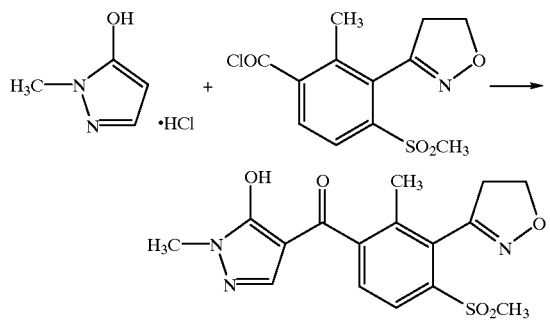

To 2.75 g of 3-(4,5-dihydroisoxazol-3-yl)-4-methylsulfonyl-2-methylbenzoic acid were added 30 ml of benzene, then 1.7 ml of thionyl chloride and a drop of pyridine to heat at reflux for 3 hours. The reaction solution was cooled down. The solvent was distilled out under reduced pressure to give 2.90 g of 3-(4,5-dihydroisoxazol-3-yl)-4-methylsulfonyl-2-methylbenzoyl chloride. Separately 0.93 g of 5-hydroxy-1-methylpyrazole hydrochloride was dissolved in 20 ml of chloroform, and 1.60 g of triethylamine was added, while cooling with ice. Into the obtained solution was added dropwise 10 ml of a chloroform solution containing 1.90 g of 3-(4,5-dihydroisoxazol-3-yl)-4-methylsulfonyl-2-methylbenzoyl chloride to stir at room temperature for 30 minutes, and 0.76 g of triethylamine and 0.16 g of acetone cyanohydrin were added to further stir overnight. The reaction solution was washed with dilute hydrochloric acid, then with a saturated sodium chloride solution, and dried over anhydrous magnesium sulfate. The solvent was distilled out under reduced pressure. Methanol was added to the residue. The obtained crystals were separated by filtration to give 1.59 g of the title compound as white crystals. m.p. 224~226° C.

Example 6

Preparation of 4-[3-(4,5-dihydroisoxazol-3-yl)-4-methylsulfonyl-2-methylbenzoyl]-1-ethyl-5-hydroxypyrazole (Compound No. 1-9)

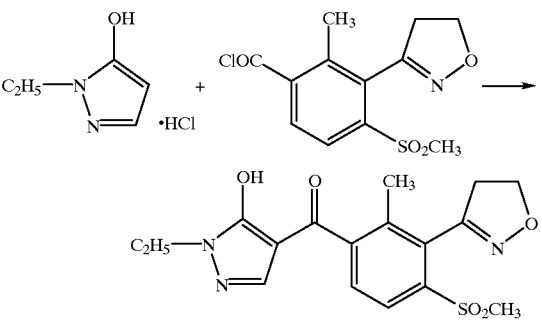

To 2.75 g of 3-(4,5-dihydroisoxazol-3-yl)-4-methylsulfonyl-2-methylbenzoic acid were added 30 ml of benzene, then 1.7 ml of thionyl chloride and a drop of pyridine to heat at reflux for 3 hours. The reaction solution was cooled down. The solvent was distilled out under reduced pressure to give 2.90 g of 3-(4,5-dihydroisoxazol-3-yl)-4-methylsulfonyl-2-methylbenzoyl chloride. Separately 0.93 g of 1-ethyl-5-hydroxypyrazole hydrochloride was dissolved in 20 ml of chloroform, and 1.60 g of triethylamine was added, while cooling with ice. Into the obtained solution was added dropwise 10 ml of a chloroform solution containing 1.90 g of 3-(4,5-dihydroisoxazol-3-yl)-4-methylsulfonyl-2-methylbenzoyl chloride to stir at room temperature for 30 minutes, and 0.76 g of triethylamine and 0.16 g of acetone cyanohydrin were added to further stir overnight. The reaction solution was washed with dilute hydrochloric acid, then with a saturated sodium chloride solution, and dried over anhydrous magnesium sulfate. The solvent was distilled out under reduced pressure. Methanol was added to the residue. The obtained crystals were separated by filtration to give 1.59 g of the title compound as white crystals. m.p. 183~184.5° C.

Example 7

Preparation of 5-benzyloxy-4-[3-(4,5-dihydroisoxazol-3-yl)-4-methylsulfonyl-2-methylbenzoyl]-1-methylpyrazole (Compound No. 1-4)

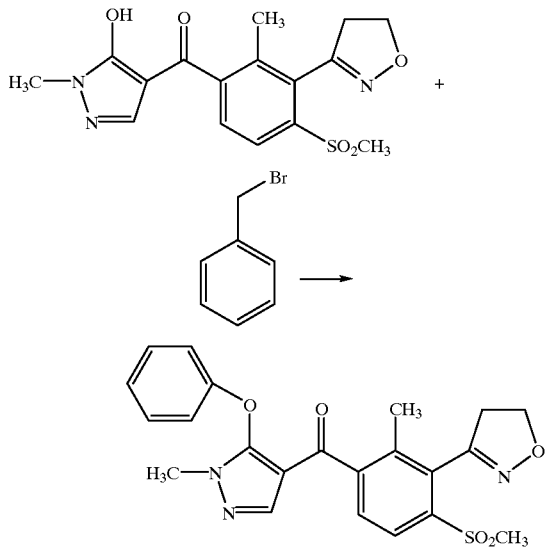

0.45 g of 4-[3-(4,5-dihydroisoxazol-3-yl)-4-methylsulfonyl-2-methylbenzoyl]-5-hydroxy-1-methylpyrazole was dissolved in 15 ml of DMF, and 0.26 g of potassium carbonate, then 0.25 g of benzyl bromide were added. The resulting solution was stirred at room temperature overnight. The reaction solution was poured into ice water, and extracted with ethyl acetate. The organic layer was washed with water, then with a saturated sodium chloride solution, and dried over anhydrous magnesium sulfate. The solvent was distilled out under reduced pressure. Methanol was added to the residue. The obtained crystals were separated by filtration to give 0.42 g of the title compound as white crystals. m.p. 151.5~153° C.

Example 8

Preparation of 4-[3-(4,5-dihydroisoxazol-3-yl)-4-methylsulfonyl-2-methylbenzoyl]-1-ethyl-5-phenacyloxypyrazole (Compound No. 1-11)

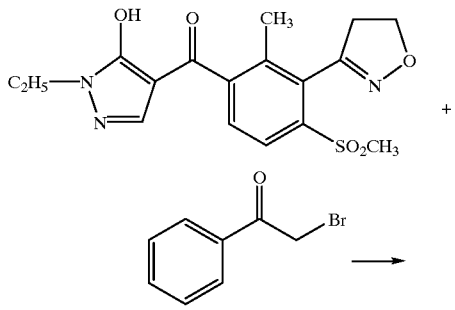

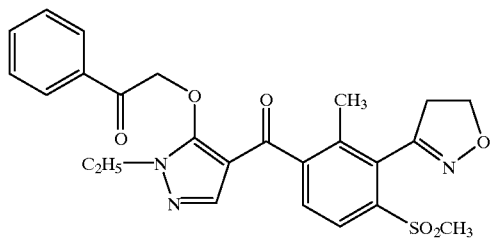

0.20 g of 4-[3-(4,5-dihydroisoxazol-3-yl)-4-methylsulfonyl-2-methylbenzoyl]-1-ethyl-5-hydroxypyrazole was dissolved in 10 ml of DMF, and 0.11 g of potassium carbonate, then 0.13 g of phenacyl bromide were added. The resulting solution was stirred at room temperature overnight. The reaction solution was poured into ice water, and extracted with ethyl acetate. The organic layer was washed with water, then with a saturated sodium chloride solution, and dried over anhydrous magnesium sulfate. The solvent was distilled out under reduced pressure. Methanol was added to the residue. The obtained crystals were separated by filtration to give 0.17 g of the title compound as white crystals. m.p. 177~179° C.

Example 9

Preparation of 1-ethyl-5-hydroxy-4-[(isoxazol-3-yl)-4-methylsulfonyl-2-methylbenzoyl]pyrazole (Compound No. 2-9)

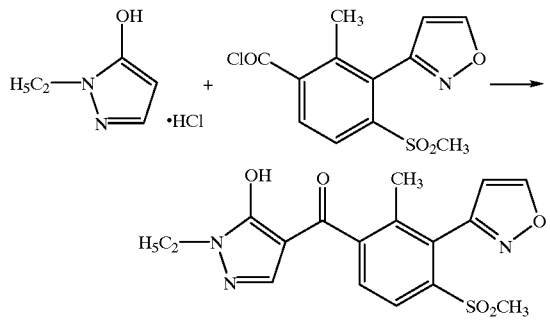

To 0.55 g of 3-(isoxazol-3-yl)-4-methylsulfonyl-2-methylbenzoic acid were added 10 ml of benzene, then 0.17 ml of thionyl chloride and a drop of triethylamine to heat at reflux for 2 hours. The reaction solution was cooled down. The solvent was distilled out under reduced pressure to give 3-(isoxazol-3-yl)-4-methylsulfonyl-2-methylbenzoyl chloride.

Separately 0.38 g of 1-ethyl-5-hydroxypyrazole hydrochloride was dissolved in 10 ml of chloroform, and 0.52 g of triethylamine was added, while cooling with ice. Into the obtained solution was added dropwise 5 ml of a chloroform solution containing the previously obtained 3-(isoxazol-3-yl)-4-methylsulfonyl-2-methylbenzoyl chloride to stir at room temperature for an hour. To the reaction mixture were added 0.26 g of triethylamine and 0.05 g of acetone cyanohydrin to further stir overnight. The reaction solution was washed with dilute hydrochloric acid, with water, then with a saturated sodium chloride solution, and dried over anhydrous magnesium sulfate. The solvent was distilled out under reduced pressure. Methanol was added to the obtained residue. The produced crystals were separated by filtration to give 0.18 g of the title compound as white crystals. m.p. 85~88° C.

Examples of the compounds of the present invention, including those in the above examples, are shown in Tables 2 and 3.

TABLE 2

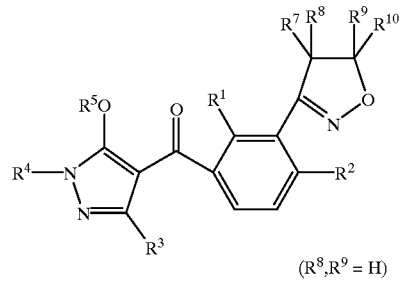

($R^8, R^9 = H$)

| Compound No. | $R^1$ | $R^2$ | $R^3$ | $R^4$ | $R^5$ | $R^7$ | $R^9$ | Melting Point (° C.) |
|---|---|---|---|---|---|---|---|---|
| 1-1 | $CH_3$ | $SO_2CH_3$ | H | $CH_3$ | H | H | H | [224–226] |
| 1-2 | $CH_3$ | $SO_2CH_3$ | H | $CH_3$ | tosyl | H | H | |
| 1-3 | $CH_3$ | $SO_2CH_3$ | H | $CH_3$ | phenacyl | H | H | |
| 1-4 | $CH_3$ | $SO_2CH_3$ | H | $CH_3$ | benzyl | H | H | [151.5–153] |
| 1-5 | $CH_3$ | $SO_2CH_3$ | $CH_3$ | $CH_3$ | H | H | H | |
| 1-6 | $CH_3$ | $SO_2CH_3$ | $CH_3$ | $CH_3$ | tosyl | H | H | |
| 1-7 | $CH_3$ | $SO_2CH_3$ | $CH_3$ | $CH_3$ | phenacyl | H | H | |
| 1-8 | $CH_3$ | $SO_2CH_3$ | $CH_3$ | $CH_3$ | benzyl | H | H | |
| 1-9 | $CH_3$ | $SO_2CH_3$ | H | $C_2H_5$ | H | H | H | [183–184.5] |
| 1-10 | $CH_3$ | $SO_2CH_3$ | H | $C_2H_5$ | tosyl | H | H | |
| 1-11 | $CH_3$ | $SO_2CH_3$ | H | $C_2H_5$ | phenacyl | H | H | [177–179] |
| 1-12 | $CH_3$ | $SO_2CH_3$ | H | $C_2H_5$ | benzyl | H | H | |
| 1-13 | $CH_3$ | $SO_2CH_3$ | H | $CH_3$ | H | $CH_3$ | H | |
| 1-14 | $CH_3$ | $SO_2CH_3$ | H | $CH_3$ | tosyl | $CH_3$ | H | |
| 1-15 | $CH_3$ | $SO_2CH_3$ | H | $CH_3$ | phenacyl | $CH_3$ | H | |
| 1-16 | $CH_3$ | $SO_2CH_3$ | H | $CH_3$ | benzyl | $CH_3$ | H | |
| 1-17 | $CH_3$ | $SO_2CH_3$ | H | $CH_3$ | H | H | $CH_3$ | [183–185] |
| 1-18 | $CH_3$ | $SO_2CH_3$ | H | $CH_3$ | tosyl | H | $CH_3$ | |
| 1-19 | $CH_3$ | $SO_2CH_3$ | H | $CH_3$ | phenacyl | H | $CH_3$ | |
| 1-20 | $CH_3$ | $SO_2CH_3$ | H | $CH_3$ | benzyl | H | $CH_3$ | |
| 1-21 | $CH_3$ | $SO_2CH_3$ | H | $CH_3$ | H | $CH_3$ | $CH_3$ | |
| 1-22 | $CH_3$ | $SO_2CH_3$ | H | $CH_3$ | tosyl | $CH_3$ | $CH_3$ | |
| 1-23 | $CH_3$ | $SO_2CH_3$ | H | $CH_3$ | phenacyl | $CH_3$ | $CH_3$ | |
| 1-24 | $CH_3$ | $SO_2CH_3$ | H | $CH_3$ | benzyl | $CH_3$ | $CH_3$ | |
| 1-25 | $CH_3$ | $SO_2CH_3$ | H | $C_2H_5$ | H | $CH_3$ | H | |
| 1-26 | $CH_3$ | $SO_2CH_3$ | H | $C_2H_5$ | tosyl | $CH_3$ | H | |
| 1-27 | $CH_3$ | $SO_2CH_3$ | H | $C_2H_5$ | phenacyl | $CH_3$ | H | |
| 1-28 | $CH_3$ | $SO_2CH_3$ | H | $C_2H_5$ | benzyl | $CH_3$ | H | |
| 1-29 | $CH_3$ | $SO_2CH_3$ | H | $C_2H_5$ | H | H | $CH_3$ | |
| 1-30 | $CH_3$ | $SO_2CH_3$ | H | $C_2H_5$ | tosyl | H | $CH_3$ | |
| 1-31 | $CH_3$ | $SO_2CH_3$ | H | $C_2H_5$ | phenacyl | H | $CH_3$ | |
| 1-32 | $CH_3$ | $SO_2CH_3$ | H | $C_2H_5$ | benzyl | H | $CH_3$ | |
| 1-33 | $CH_3$ | $SO_2CH_3$ | H | $C_2H_5$ | H | $CH_3$ | $CH_3$ | |
| 1-34 | $CH_3$ | $SO_2CH_3$ | H | $C_2H_5$ | tosyl | $CH_3$ | $CH_3$ | |
| 1-35 | $CH_3$ | $SO_2CH_3$ | H | $C_2H_5$ | phenacyl | $CH_3$ | $CH_3$ | |
| 1-36 | $CH_3$ | $SO_2CH_3$ | H | $C_2H_5$ | benzyl | $CH_3$ | $CH_3$ | |
| 1-37 | $CH_3$ | $SO_2CH_3$ | $CH_3$ | $CH_3$ | H | $CH_3$ | $CH_3$ | |
| 1-38 | $CH_3$ | $SO_2CH_3$ | $CH_3$ | $CH_3$ | tosyl | $CH_3$ | $CH_3$ | |
| 1-39 | $CH_3$ | $SO_2CH_3$ | $CH_3$ | $CH_3$ | phenacyl | $CH_3$ | $CH_3$ | |
| 1-40 | $CH_3$ | $SO_2CH_3$ | $CH_3$ | $CH_3$ | benzyl | $CH_3$ | $CH_3$ | |
| 1-41 | $CH_3$ | $SO_2CH_3$ | $CH_3$ | $CH_3$ | H | H | i-Pr | |
| 1-42 | $C_2H_5$ | $SO_2CH_3$ | H | $CH_3$ | H | H | H | |
| 1-43 | $C_2H_5$ | $SO_2CH_3$ | H | $CH_3$ | tosyl | H | H | |
| 1-44 | $C_2H_5$ | $SO_2CH_3$ | H | $CH_3$ | phenacyl | H | H | |
| 1-45 | $C_2H_5$ | $SO_2C_2H_5$ | H | $CH_3$ | benzyl | H | H | |
| 1-46 | $CH_3$ | $SO_2C_2H_5$ | H | $CH_3$ | H | H | H | |
| 1-47 | $CH_3$ | $SO_2C_2H_5$ | H | $CH_3$ | tosyl | H | H | |
| 1-48 | $CH_3$ | $SO_2C_2H_5$ | $CH_3$ | $CH_3$ | phenacyl | H | H | |
| 1-49 | $CH_3$ | $SO_2C_2H_5$ | $CH_3$ | $CH_3$ | benzyl | H | H | |
| 1-50 | $CH_3$ | $SO_2C_3H_7$ | H | $CH_3$ | H | H | $CH_3$ | |
| 1-51 | $CH_3$ | $SO_2C_3H_7$ | H | $CH_3$ | tosyl | H | $CH_3$ | |
| 1-52 | $CH_3$ | $SO_2C_3H_7$ | H | $CH_3$ | phenacyl | H | $CH_3$ | |
| 1-53 | $CH_3$ | $SO_2C_3H_7$ | H | $CH_3$ | benzyl | H | $CH_3$ | |
| 1-54 | $CH_3$ | $SO_2$i-Pr | H | $CH_3$ | H | $CH_3$ | H | |
| 1-55 | $CH_3$ | $SO_2$i-Pr | H | $CH_3$ | tosyl | $CH_3$ | H | |
| 1-56 | $CH_3$ | $SO_2$i-Pr | H | $CH_3$ | phenacyl | $CH_3$ | H | |
| 1-57 | $CH_3$ | $SO_2$i-Pr | H | $CH_3$ | benzyl | $CH_3$ | H | |
| 1-58 | $CH_3$ | $SO_2$t-Bu | H | $CH_3$ | H | H | H | |

TABLE 2-continued

| | $R^1$ | $R^2$ | $R^3$ | $R^4$ | $R^5$ | | $R^8$ | $R^9$ | $R^{10}$ |
|---|---|---|---|---|---|---|---|---|---|
| 1-59 | $CH_3$ | $SO_2CH_3$ | H | Pr | H | | H | H | |
| 1-60 | $CH_3$ | $SO_2CH_3$ | H | i-Pr | tosyl | | H | H | |
| 1-61 | $CH_3$ | $SO_2CH_3$ | H | t-Bu | phenacyl | | H | H | |
| 1-62 | $CH_3$ | $SO_2CH_3$ | H | Pr | benzyl | | H | H | |
| 1-63 | $CH_3$ | $SO_2CH_3$ | H | $CH_3$ | 2-Cl-benzyl | | H | H | |
| 1-64 | $CH_3$ | $SO_2CH_3$ | H | $CH_3$ | 4-Me-benzyl | | H | H | |
| 1-65 | $CH_3$ | $SO_2CH_3$ | H | $CH_3$ | 3-OMe-phenacyl | | H | H | |

| Compound No. | $R^1$ | $R^2$ | $R^3$ | $R^4$ | $R^5$ | $R^7$ | $R^8$ | $R^9$ | $R^{10}$ |
|---|---|---|---|---|---|---|---|---|---|
| 1-66 | $CH_3$ | $SO_2CH_3$ | H | $CH_3$ | H | $CH_3$ | $CH_3$ | H | H |
| 1-67 | $CH_3$ | $SO_2CH_3$ | H | $CH_3$ | tosyl | $CH_3$ | $CH_3$ | H | H |
| 1-68 | $CH_3$ | $SO_2CH_3$ | H | $CH_3$ | phenacyl | $CH_3$ | $CH_3$ | H | H |
| 1-69 | $CH_3$ | $SO_2CH_3$ | H | $CH_3$ | benzyl | $CH_3$ | $CH_3$ | H | H |
| 1-70 | $CH_3$ | $SO_2CH_3$ | H | $CH_3$ | H | $CH_3$ | $C_2H_5$ | H | H |
| 1-71 | $CH_3$ | $SO_2CH_3$ | H | $CH_3$ | tosyl | $CH_3$ | $C_2H_5$ | H | H |
| 1-72 | $CH_3$ | $SO_2CH_3$ | H | $CH_3$ | phenacyl | $CH_3$ | $C_2H_5$ | H | H |
| 1-73 | $CH_3$ | $SO_2CH_3$ | H | $CH_3$ | benzyl | $CH_3$ | $C_2H_5$ | H | H |
| 1-74 | $CH_3$ | $SO_2CH_3$ | H | $CH_3$ | H | $C_2H_5$ | $C_2H_5$ | H | H |
| 1-75 | $CH_3$ | $SO_2CH_3$ | H | $CH_3$ | tosyl | $C_2H_5$ | $C_2H_5$ | H | H |
| 1-76 | $CH_3$ | $SO_2CH_3$ | H | $CH_3$ | phenacyl | $C_2H_5$ | $C_2H_5$ | H | H |
| 1-77 | $CH_3$ | $SO_2CH_3$ | H | $CH_3$ | benzyl | $C_2H_5$ | $C_2H_5$ | H | H |
| 1-78 | $CH_3$ | $SO_2CH_3$ | H | $CH_3$ | H | H | H | $CH_3$ | $CH_3$ |
| 1-79 | $CH_3$ | $SO_2CH_3$ | H | $CH_3$ | tosyl | H | H | $CH_3$ | $CH_3$ |
| 1-80 | $CH_3$ | $SO_2CH_3$ | H | $CH_3$ | phenacyl | H | H | $CH_3$ | $CH_3$ |
| 1-81 | $CH_3$ | $SO_2CH_3$ | H | $CH_3$ | benzyl | H | H | $CH_3$ | $CH_3$ |
| 1-82 | $CH_3$ | $SO_2CH_3$ | H | $CH_3$ | H | H | H | $CH_3$ | $C_2H_5$ |
| 1-83 | $CH_3$ | $SO_2CH_3$ | H | $CH_3$ | tosyl | H | H | $CH_3$ | $C_2H_5$ |
| 1-84 | $CH_3$ | $SO_2CH_3$ | H | $CH_3$ | phenacyl | H | H | $CH_3$ | $C_2H_5$ |
| 1-85 | $CH_3$ | $SO_2CH_3$ | H | $CH_3$ | benzyl | H | H | $CH_3$ | $C_2H_5$ |
| 1-86 | $CH_3$ | $SO_2CH_3$ | H | $CH_3$ | H | H | H | $C_2H_5$ | $C_2H_5$ |
| 1-87 | $CH_3$ | $SO_2CH_3$ | H | $CH_3$ | tosyl | H | H | $C_2H_5$ | $C_2H_5$ |
| 1-88 | $CH_3$ | $SO_2CH_3$ | H | $CH_3$ | phenacyl | H | H | $C_2H_5$ | $C_2H_5$ |
| 1-89 | $CH_3$ | $SO_2CH_3$ | H | $CH_3$ | benzyl | H | H | $C_2H_5$ | $C_2H_5$ |

TABLE 3

| Compound No. | $R^1$ | $R^2$ | $R^3$ | $R^4$ | $R^5$ | $R^7$ ($R^8$) | $R^9$ ($R^{10}$) | Melting Point (° C.) |
|---|---|---|---|---|---|---|---|---|
| 2-1 | $CH_3$ | $SO_2CH_3$ | H | $CH_3$ | H | H | H | |
| 2-2 | $CH_3$ | $SO_2CH_3$ | H | $CH_3$ | tosyl | H | H | |
| 2-3 | $CH_3$ | $SO_2CH_3$ | H | $CH_3$ | phenacyl | H | H | |
| 2-4 | $CH_3$ | $SO_2CH_3$ | H | $CH_3$ | benzyl | H | H | |
| 2-5 | $CH_3$ | $SO_2CH_3$ | $CH_3$ | $CH_3$ | H | H | H | |
| 2-6 | $CH_3$ | $SO_2CH_3$ | $CH_3$ | $CH_3$ | tosyl | H | H | |
| 2-7 | $CH_3$ | $SO_2CH_3$ | $CH_3$ | $CH_3$ | phenacyl | H | H | |
| 2-8 | $CH_3$ | $SO_2CH_3$ | $CH_3$ | $CH_3$ | benzyl | H | H | |
| 2-9 | $CH_3$ | $SO_2CH_3$ | H | $C_2H_5$ | H | H | H | [85–88] |
| 2-10 | $CH_3$ | $SO_2CH_3$ | H | $C_2H_5$ | tosyl | H | H | |
| 2-11 | $CH_3$ | $SO_2CH_3$ | H | $C_2H_5$ | phenacyl | H | H | |
| 2-12 | $CH_3$ | $SO_2CH_3$ | H | $C_2H_5$ | benzyl | H | H | |
| 2-13 | $CH_3$ | $SO_2CH_3$ | H | $CH_3$ | H | $CH_3$ | H | |
| 2-14 | $CH_3$ | $SO_2CH_3$ | H | $CH_3$ | tosyl | $CH_3$ | H | |
| 2-15 | $CH_3$ | $SO_2CH_3$ | H | $CH_3$ | phenacyl | $CH_3$ | H | |
| 2-16 | $CH_3$ | $SO_2CH_3$ | H | $CH_3$ | benzyl | $CH_3$ | H | |
| 2-17 | $CH_3$ | $SO_2CH_3$ | H | $CH_3$ | H | H | $CH_3$ | [248–251] |
| 2-18 | $CH_3$ | $SO_2CH_3$ | H | $CH_3$ | tosyl | H | $CH_3$ | |
| 2-19 | $CH_3$ | $SO_2CH_3$ | H | $CH_3$ | phenacyl | H | $CH_3$ | |

TABLE 3-continued $$\text{Structure: } R^5O\text{-pyrazole}(R^4,R^3)\text{-C(=O)-phenyl}(R^1,R^2)\text{-isoxazoline}(R^7(R^8),R^9(R^{10}))$$

| Compound No. | $R^1$ | $R^2$ | $R^3$ | $R^4$ | $R^5$ | $R^7$ ($R^8$) | $R^9$ ($R^{10}$) | Melting Point (° C.) |
|---|---|---|---|---|---|---|---|---|
| 2-20 | CH₃ | SO₂CH₃ | H | CH₃ | benzyl | H | CH₃ | |
| 2-21 | CH₃ | SO₂CH₃ | H | CH₃ | H | CH₃ | CH₃ | |
| 2-22 | CH₃ | SO₂CH₃ | H | CH₃ | tosyl | CH₃ | CH₃ | |
| 2-23 | CH₃ | SO₂CH₃ | H | CH₃ | phenacyl | CH₃ | CH₃ | |
| 2-24 | CH₃ | SO₂CH₃ | H | CH₃ | benzyl | CH₃ | CH₃ | |
| 2-25 | CH₃ | SO₂CH₃ | H | C₂H₅ | H | CH₃ | H | |
| 2-26 | CH₃ | SO₂CH₃ | H | C₂H₅ | tosyl | CH₃ | H | |
| 2-27 | CH₃ | SO₂CH₃ | H | C₂H₅ | phenacyl | CH₃ | H | |
| 2-28 | CH₃ | SO₂CH₃ | H | C₂H₅ | benzyl | CH₃ | H | |
| 2-29 | CH₃ | SO₂CH₃ | H | C₂H₅ | H | H | CH₃ | |
| 2-30 | CH₃ | SO₂CH₃ | H | C₂H₅ | tosyl | H | CH₃ | |
| 2-31 | CH₃ | SO₂CH₃ | H | C₂H₅ | phenacyl | H | CH₃ | |
| 2-32 | CH₃ | SO₂CH₃ | H | C₂H₅ | benzyl | H | CH₃ | |
| 2-33 | CH₃ | SO₂CH₃ | H | C₂H₅ | H | CH₃ | CH₃ | |
| 2-34 | CH₃ | SO₂CH₃ | H | C₂H₅ | tosyl | CH₃ | CH₃ | |
| 2-35 | CH₃ | SO₂CH₃ | H | C₂H₅ | phenacyl | CH₃ | CH₃ | |
| 2-36 | CH₃ | SO₂CH₃ | H | C₂H₅ | benzyl | CH₃ | CH₃ | |
| 2-37 | CH₃ | SO₂CH₃ | CH₃ | CH₃ | H | CH₃ | CH₃ | |
| 2-38 | CH₃ | SO₂CH₃ | CH₃ | CH₃ | tosyl | CH₃ | CH₃ | |
| 2-39 | CH₃ | SO₂CH₃ | CH₃ | CH₃ | phenacyl | CH₃ | CH₃ | |
| 2-40 | CH₃ | SO₂CH₃ | CH₃ | CH₃ | benzyl | CH₃ | CH₃ | |
| 2-41 | CH₃ | SO₂CH₃ | CH₃ | CH₃ | H | H | i-Pr | |
| 2-42 | C₂H₅ | SO₂CH₃ | H | CH₃ | H | H | H | |
| 2-43 | C₂H₅ | SO₂CH₃ | H | CH₃ | tosyl | H | H | |
| 2-44 | C₂H₅ | SO₂CH₃ | H | CH₃ | phenacyl | H | H | |
| 2-45 | C₂H₅ | SO₂C₂H₅ | H | CH₃ | benzyl | H | H | |
| 2-46 | CH₃ | SO₂C₂H₅ | H | CH₃ | H | H | H | |
| 2-47 | CH₃ | SO₂C₂H₅ | H | CH₃ | tosyl | H | H | |
| 2-48 | CH₃ | SO₂C₂H₅ | CH₃ | CH₃ | phenacyl | H | H | |
| 2-49 | CH₃ | SO₂C₂H₅ | CH₃ | CH₃ | benzyl | H | H | |
| 2-50 | CH₃ | SO₂C₃H₇ | H | CH₃ | H | H | CH₃ | |
| 2-51 | CH₃ | SO₂C₃H₇ | H | CH₃ | tosyl | H | CH₃ | |
| 2-52 | CH₃ | SO₂C₃H₇ | H | CH₃ | phenacyl | H | CH₃ | |
| 2-53 | CH₃ | SO₂C₃H₇ | H | CH₃ | benzyl | H | CH₃ | |
| 2-54 | CH₃ | SO₂i-Pr | H | CH₃ | H | CH₃ | H | |
| 2-55 | CH₃ | SO₂i-Pr | H | CH₃ | tosyl | CH₃ | H | |
| 2-56 | CH₃ | SO₂i-Pr | H | CH₃ | phenacyl | CH₃ | H | |
| 2-57 | CH₃ | SO₂i-Pr | H | CH₃ | benzyl | CH₃ | H | |
| 2-58 | CH₃ | SO₂t-Bu | H | CH₃ | H | H | H | |
| 2-59 | CH₃ | SO₂CH₃ | H | Pr | H | H | H | |
| 2-60 | CH₃ | SO₂CH₃ | H | i-Pr | tosyl | H | H | |
| 2-61 | CH₃ | SO₂CH₃ | H | t-Bu | phenacyl | H | H | |
| 2-62 | CH₃ | SO₂CH₃ | H | Pr | benzyl | H | H | |
| 2-63 | CH₃ | SO₂CH₃ | H | CH₃ | 2-Cl-benzyl | H | H | |
| 2-64 | CH₃ | SO₂CH₃ | H | CH₃ | 4-Me-benzyl | H | H | |
| 2-65 | CH₃ | SO₂CH₃ | H | CH₃ | 3-OMe-phenacyl | H | H | |

Herbicide

Some examples of formulations regarding to the herbicides of the present invention are described in the following. Active ingredients, additives and addition ratios are not limited to the scope described in these examples and can be changed over a wide range. In the example formulations, "part(s)" means "part(s) by weight".

Example 10

Wettable Powder Formulation

| | |
|---|---|
| Compound of the present invention | 20 parts |
| White carbon | 20 parts |
| Diatomaceous earth | 52 parts |
| Sodium alkylsulfate | 8 parts |

These materials are uniformly mixed and finely ground to give wettable powder containing 20% of the active ingredient.

Example 11
Emulsifiable Concentrate Formulation

| | |
|---|---|
| Compound of the present invention | 20 parts |
| Xylene | 55 parts |
| Dimethyl formamide | 15 parts |
| Polyoxyethylene phenyl ether | 10 parts |

These materials are mixed and dissolved to give an emulsifiable concentrate containing 20% of the active ingredient.

Example 12
Granular Formulation

| | |
|---|---|
| Compound of the present invention | 5 parts |
| Talc | 40 parts |
| Clay | 38 parts |
| Bentonite | 10 parts |
| Sodium alkylsulfate | 7 parts |

These materials are uniformly mixed, finely ground, and granulated to give granules of 0.5~1.0 mm in diameter and containing 5% of the active ingredient.

A test example regarding to the effect of the herbicides of the present invention is described in the following.

The herbicidal effect was evaluated in accordance with the following evaluation criteria and represented by herbicidal index.

Evaluation Criteria

| Weeds killed in % | Herbicidal index |
|---|---|
| 0% | 0 |
| 20 ~ 29% | 2 |
| 40 ~ 49% | 4 |
| 60 ~ 69% | 6 |
| 80 ~ 89% | 8 |
| 100% | 10 |

Values of 1, 3, 5, 7 and 9 mean values between 0 and 2, 2 and 4, 4 and 6, 6 and 8 and 8 and 10, respectively.
Weeks killed (%)=(Fresh weight of shoots in a non-treated plot−Fresh weight of shoots in a treated plot) Fresh weight of shoots in a non-treated plot×100

Test Example 1
Foliage Treatment

Velvetleaf, pigweed, cocklebur, giant foxtail and corn were each seeded on the surface of soil in a 200cm² pot, lightly covered with soil, and grew in a greenhouse. The emulsifiable concentrate described in Example 11 was diluted with water. When each plant grew 5–25 cm high, the dilute emulsion was sprayed over the foliage with a small spray with an amount equivalent to 1000 liter/ha so that the active ingredient was applied at a prescribed amount. After 3 weeks, chemical injuries of the crop and herbicidal effect on the weeds were evaluated according to the above evaluation criteria. The results are shown in Table 4.

Industrial Use

TABLE 4

| Compound No. | Dosage (g/ha) | Velvet leaf | Pigweed | Cocklebur | Giant foxtail | Corn |
|---|---|---|---|---|---|---|
| 1-1 | 63 | 10 | 10 | 10 | 10 | 0 |
| 1-9 | 63 | 9 | 10 | 10 | 10 | 0 |
| 1-17 | 63 | 9 | 10 | 10 | 10 | 0 |
| A | 63 | 8 | 10 | 8 | 10 | 9 |

Compound A:

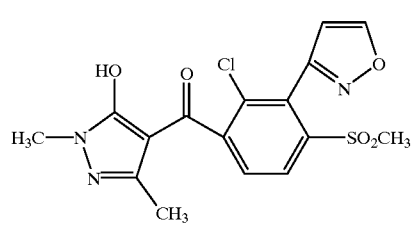

The compounds of the present invention can be used as a selective herbicide of corn and the like, and are industrially advantageous as mentioned above.

What is claimed:

1. A compound represented by the formula I

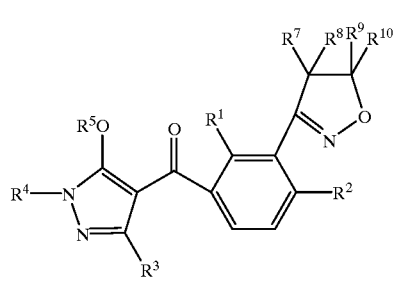

wherein $R^1$ is a $C_1$–$C_6$ alkyl group; $R^2$ is a $C_1$–$C_6$ alkylthio group or a $C_1$–$C_6$ alkylsulfonyl group; $R^3$ and $R^4$ are each independently hydrogen or a $C_1$–$C_6$ alkyl group; $R^5$ is hydrogen or a group selected from the group represented by the following formula

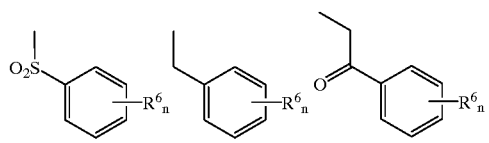

wherein $R^6$ is halogen, a $C_1$–$C_6$ alkyl group or a $C_1$–$C_6$ alkoxy group; and n is 0, 1, 2, 3, 4 or 5; $R^7$, $R^8$, $R^9$ and $R^{10}$ are each independently hydrogen or a $C_1$–$C_6$ alkyl group; and $R^7$ or $R^8$ and $R^9$ or $R^{11}$ may form a single bond, or a salt thereof.

2. A herbicide characterized by containing one or more compounds represented by formula I

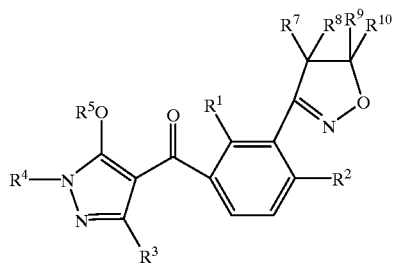

wherein $R^1$ is a $C_1-C_6$ alkyl group; $R^2$ is a $C_1-C_6$ alkylthio group or a $C_1-C_6$ alkylsulfonyl group; $R^3$ and $R^4$ are each independently hydrogen or a $C_1-C_6$ alkyl group; $R^5$ is hydrogen or a group selected from the group represented by the following formula

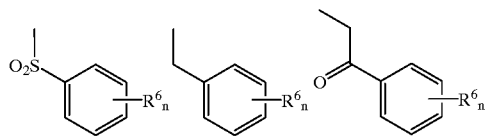

wherein $R^6$ is halogen, a $C_1-C_6$ alkyl group or a $C_1-C_6$ alkoxy group; and n is 0, 1, 2, 3, 4 or 5; $R^7$, $R^8$, $R^9$ and $R^{10}$ are each independently hydrogen or a $C_1-C_6$ alkyl group; and $R^7$ or $R^8$ and $R^9$ or $R^{10}$ may form a single bond or salts thereof, as active ingredients.

3. A compound represented by the formula (1)

(1)

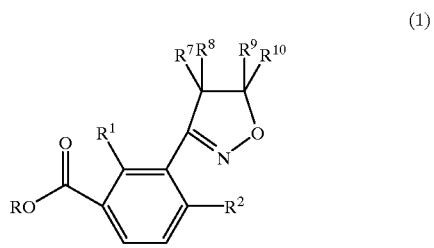

wherein $R^1$ is a $C_1-C_6$ alkyl group; $R^2$ is a $C_1-C_6$ alkylthio group or a $C_1-C_6$ alkylsulfonyl group and $R^7$, $R^8$, $R^9$ and $R^{10}$ are each independently hydrogen or a $C_1-C_6$ alkyl group; and $R^7$ or $R^8$, and $R^9$ or $R^{10}$ may form a single bond; R is hydrogen or a $C_1-C_6$ alkyl group).

* * * * *

UNITED STATES PATENT AND TRADEMARK OFFICE
CERTIFICATE OF CORRECTION

PATENT NO : 6,147,031
DATED : November 14, 2000
INVENTOR(S) : Hiroyuki Adachi, et al.

It is certified that error appears in the above-identified patent and that said Letters Patent are hereby corrected as shown below:

On title page, item 54 Title
 replace "BENZOYLPYRAZOLE COMPOUNDS, INTERMEDIATE
   PREPARING THEREOFE AND HERBICIDES"
 with --NOVEL BENZOYLPYRAZOLE COMPOUNDS, INTERMEDIATE
   PREPARING THEREFOR AND HERBICIDES--

On titel pge, item 75 Inventors
 replace "Hiroyuki Adachi; Katsuroni Tanaka,
   both of Odawara; Akihiro Takahashi
   Ohi-machi; Masami Koguchi,
   Odawara, all of Japan"
 with --**Hiroyuki Adachi; Katsunori Tanaka;
   Akihiro Takahashi; Masami Koguchi,**
   all of Kanagawa, Japan--

Signed and Sealed this

Fifteenth Day of May, 2001

Attest:

NICHOLAS P. GODICI

Attesting Officer

Acting Director of the United States Patent and Trademark Office